United States Patent
Lapsley et al.

(10) Patent No.: US 9,483,764 B1
(45) Date of Patent: *Nov. 1, 2016

(54) BIOMETRIC FINANCIAL TRANSACTION SYSTEM AND METHOD

(71) Applicant: Open Invention Network LLC, Durham, NC (US)

(72) Inventors: Philip D. Lapsley, Oakland, CA (US); Philip J. Gioia, Corte Madera, CA (US); Michael Kleeman, Corte Madera, CA (US)

(73) Assignee: Open Invention Network, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/150,448

(22) Filed: Jan. 8, 2014

Related U.S. Application Data

(63) Continuation of application No. 13/859,850, filed on Apr. 10, 2013, now Pat. No. 8,630,933, which is a continuation of application No. 13/284,219, filed on Oct. 28, 2011, now Pat. No. 8,452,680, which is a (Continued)

(51) Int. Cl.
*G06Q 20/40* (2012.01)
*G06Q 20/32* (2012.01)

(52) U.S. Cl.
CPC ........ *G06Q 20/40145* (2013.01); *G06Q 20/32* (2013.01)

(58) Field of Classification Search
CPC .......... G07C 9/00158; G07C 9/00087; G07C 9/00103; G06F 21/32; G06F 21/34; G06F 2211/008; G06Q 20/04; G06Q 20/341; G06Q 20/02; G06Q 20/4014; G06Q 20/10; G06Q 20/40; G06Q 20/40145; G06Q 20/00; G06Q 20/12; G06Q 20/18; G06Q 20/347; G06Q 20/3821; G06Q 40/02; G06Q 50/22; G06Q 10/08; G06Q 20/023; G06Q 20/042; G06Q 20/105; G06Q 20/206; G06Q 20/3674; G06Q 20/385; G06Q 20/389; G06Q 20/401; G06Q 20/40975; G06Q 30/02; G06Q 30/04; G06Q 40/00; G06Q 50/24; G07F 7/1008; G07F 7/10; G07F 7/1075; H04L 63/0428; H04L 9/3231; B60W 2550/402
USPC .............. 705/44, 58, 75; 235/379, 380, 487; 382/115; 340/5.1, 5.82; 380/258, 286; 713/159; 702/104; 307/10.5; 455/456.1

See application file for complete search history.

(56) References Cited

U.S. PATENT DOCUMENTS

| | | | | |
|---|---|---|---|---|
| 5,485,510 A | * | 1/1996 | Colbert | G06Q 20/02 235/380 |
| 5,546,523 A | * | 8/1996 | Gatto | G06Q 20/10 235/379 |

(Continued)

*Primary Examiner* — Behrang Badii
*Assistant Examiner* — Sanjeev Malhotra
(74) *Attorney, Agent, or Firm* — Haynes and Boone, LLP

(57) ABSTRACT

Tokenless biometric authorization of transaction between a consumer and a merchant uses an identicator and an access device. A consumer registers with the identicator a biometric sample taken from the consumer. The consumer and merchant establish communications via the access device. The merchant proposes a transaction to the consumer via the access device. The access device communicates to the merchant associated with the access device. After the consumer and merchant have agreed on the transaction, the consumer and the identicator use the access device to establish communications. The access device communicates to the identicator the code associated with the access device. The identicator compares biometric sample from the consumer with registered biometric sample. Upon successful identification, the identicator forwards information regarding the consumer to the merchant. These steps accomplish a biometrically authorized electronic financial transaction without the consumer having to present any personalized man-made memory tokens.

21 Claims, 2 Drawing Sheets

Related U.S. Application Data continuation of application No. 13/108,703, filed on May 16, 2011, now Pat. No. 8,073,756, which is a continuation of application No. 12/423,628, filed on Apr. 14, 2009, now Pat. No. 7,970,678, which is a continuation of application No. 09/871,241, filed on May 30, 2001, now Pat. No. 7,565,329.

(60) Provisional application No. 60/208,680, filed on May 31, 2000.

(56) References Cited

U.S. PATENT DOCUMENTS

| | | | | |
|---|---|---|---|---|
| 5,598,474 | A * | 1/1997 | Johnson | G06F 21/32 235/380 |
| 5,615,277 | A * | 3/1997 | Hoffman | G06F 21/32 382/115 |
| 5,719,950 | A * | 2/1998 | Osten | A61B 5/0205 340/5.82 |
| 5,770,849 | A * | 6/1998 | Novis | G06K 7/0013 235/487 |
| 5,876,926 | A * | 3/1999 | Beecham | A61B 5/117 382/115 |
| 5,910,988 | A * | 6/1999 | Ballard | G06K 9/00973 705/75 |
| 5,943,423 | A * | 8/1999 | Muftic | G06F 21/33 705/58 |
| 6,028,950 | A * | 2/2000 | Merjanian | G06F 21/32 382/115 |
| 6,070,141 | A * | 5/2000 | Houvener | G06Q 20/04 235/380 |
| 6,154,727 | A * | 11/2000 | Karp | G06Q 10/08 455/456.1 |
| 6,208,746 | B1 * | 3/2001 | Musgrave | G06Q 20/04 340/5.1 |
| 6,219,439 | B1 * | 4/2001 | Burger | G06F 21/32 235/380 |
| 6,225,890 | B1 * | 5/2001 | Murphy | B60R 25/012 307/10.5 |
| 6,317,834 | B1 * | 11/2001 | Gennaro | G06F 21/32 380/286 |
| 6,928,546 | B1 * | 8/2005 | Nanavati | G07C 9/00087 713/159 |
| 7,133,792 | B2 * | 11/2006 | Murakami | G06K 9/00536 702/104 |
| 2001/0033661 | A1 * | 10/2001 | Prokoski | H04L 9/3297 380/258 |
| 2001/0051924 | A1 * | 12/2001 | Uberti | G06Q 20/02 705/44 |

* cited by examiner

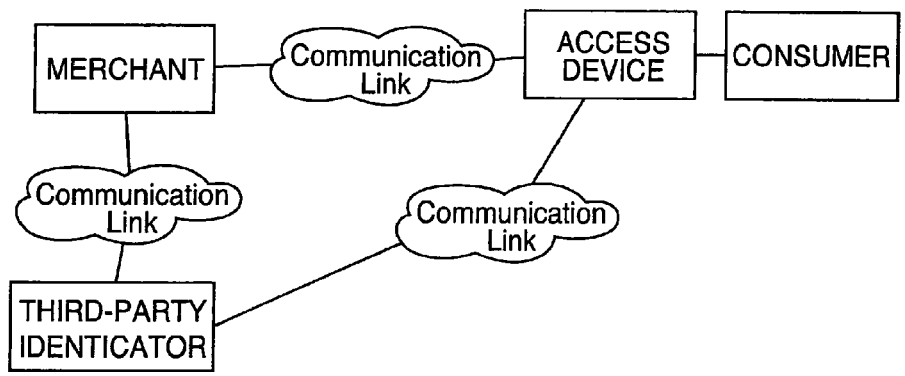
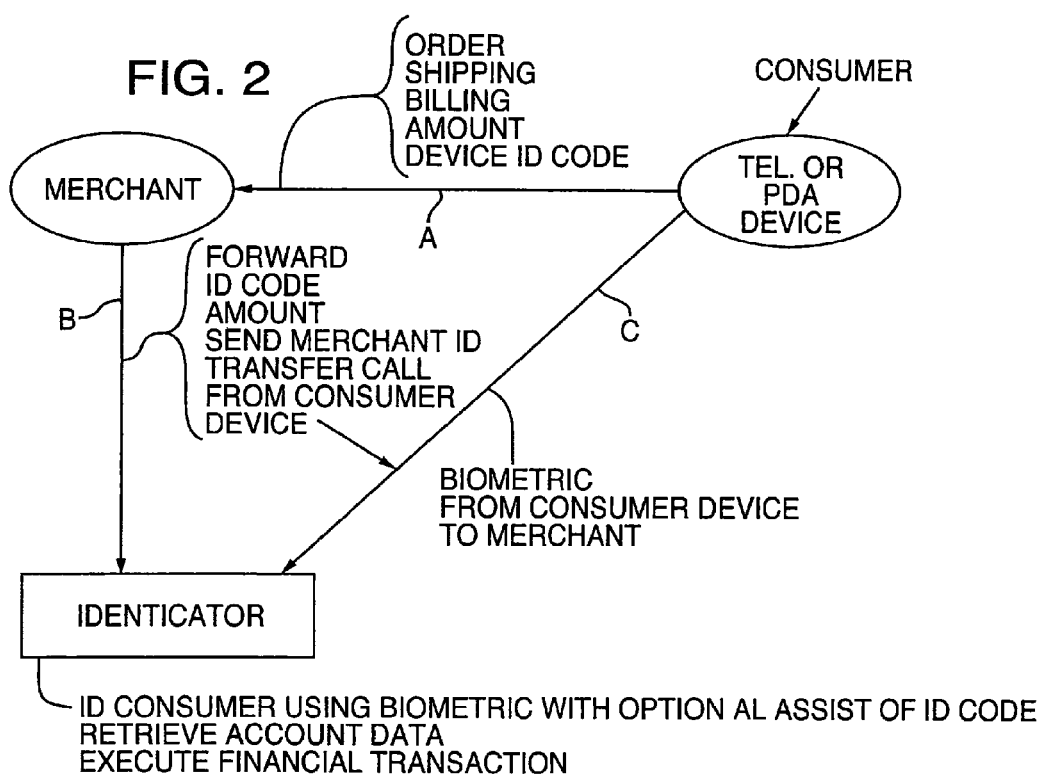

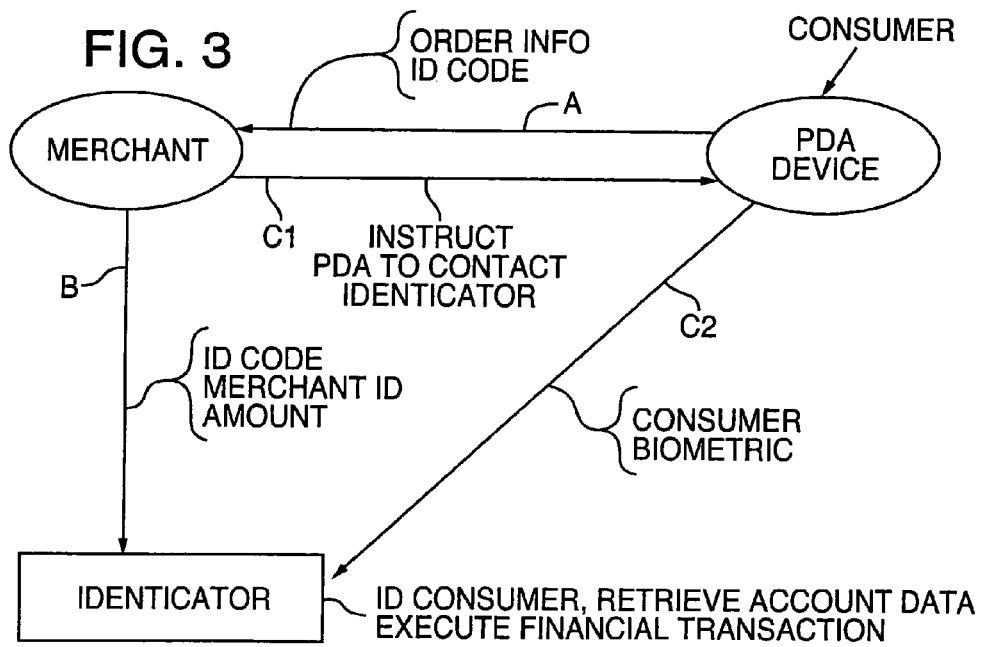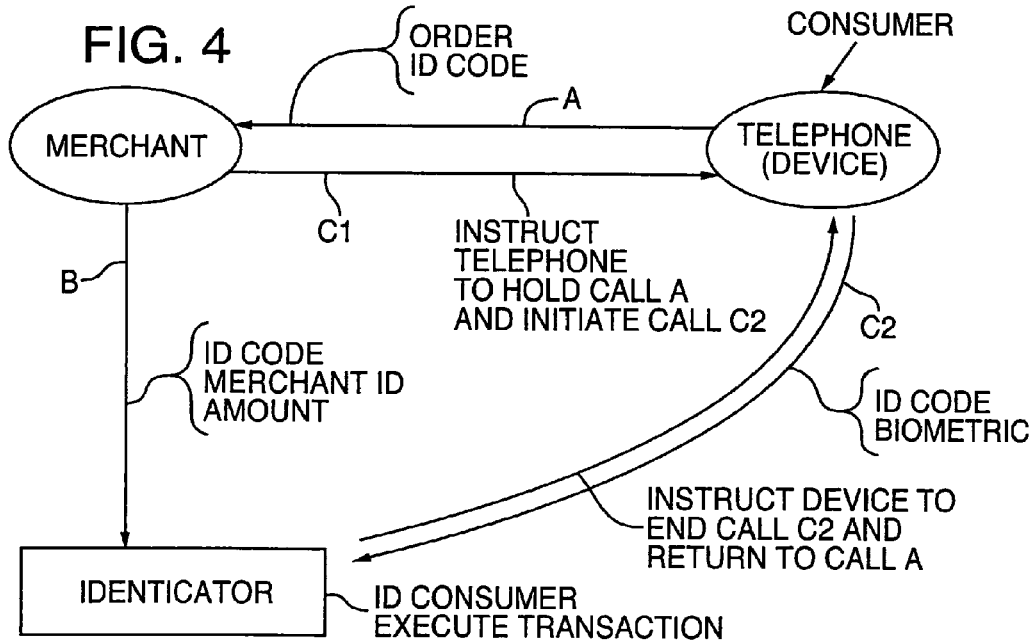

BIOMETRIC FINANCIAL TRANSACTION SYSTEM AND METHOD

CROSS-REFERENCE

This application is a continuation of U.S. application Ser. No. 13/859,850, filed Apr. 10, 2013, now U.S. Pat. No. 8,630,933, issued on Jan. 14, 2014, which is a continuation of U.S. application Ser. No. 13/284,219, filed Oct. 28, 2011, now issued U.S. Pat. No. 8,452,680, issued on May 28, 3013, which is a continuation of U.S. application Ser. No. 13/108,703, filed May 16, 2011, now issued U.S. Pat. No. 8,073,756, issued on Dec. 6, 2011, which is a continuation of U.S. application Ser. No. 12/423,628, filed Apr. 14, 2009, now issued U.S. Pat. No. 7,970,678, issued on Jun. 28, 2011, which is a division of U.S. Pat. No. 7,565,329, filed May 30, 2001, which claims the benefit of U.S. provisional application Ser. No. 60/208,680, filed May 31, 2000, herein incorporated by reference.

FIELD OF THE INVENTION

This invention relates to the field of tokenless biometric financial transactions. Specifically, this invention is directed towards a system and method for processing tokenless financial transactions using a wired or wireless communication system such as a conventional telephone, a cellular telephone, or a wireless personal digital assistant (PDA) wherein a biometric, such as a finger image or voice print, is used to authorize the transaction.

BACKGROUND OF THE INVENTION

There is an increasing need for consumers to be able to conveniently and securely purchase goods and services over the telephone (be it wired or wireless) or via a wireless PDA such as a Palm Pilot.

Conventionally, purchases made over the telephone are accomplished via the use of a credit card. The consumer calls the merchant, places an order for the appropriate goods and services, and then chooses a credit card with which to pay for the transaction. The consumer then reads the account number and expiration date off the credit card to the customer service representative at the merchant, who copies this information down and uses it to charge the account.

Purchases made using a wireless PDA or other device for accessing the Internet follow a similar pattern: the consumer connects to the merchant's web site, places an order, and then fills in a "form" with credit card account number and expiration information. The merchant's computer system uses this information to charge the credit card account.

There are numerous problems with this conventional approach. First, the system is inconvenient for the consumer, in that the consumer must recite or enter a significant amount of information. Second, the system is insecure, in that the credit card account information is generally transmitted "in the clear," making it subject to loss or compromise via interception. Third, the system is inflexible, in that the only payment mechanism that lends itself to use is the credit card; it is difficult, for example, to use one's checking account to pay via telephone.

A fourth problem is that transactions made without the card being physically present (as in the case of a telephone or Internet order) are charged a higher "discount rate" than transactions where the card is present. The discount rate is the amount that the credit card associations, issuing banks, acquiring banks, and third-party transaction processors collectively charge the merchant on each transaction, generally expressed as a percentage of the gross transaction amount. Discount rates of 3%-5% for card-not-present transactions are common.

The fifth, and perhaps largest, problem is that the consumer can repudiate the transaction at a later date, leaving the merchant liable for the amount of the transaction. That is, a consumer can order goods or services via telephone or the Internet, pay using his or her credit card, and then later dispute the transaction. In the event of a dispute, credit card association rules place the burden on the merchant to produce a signed receipt showing that the customer authorized the transaction. Of course, in the case where the order took place over the telephone or the Internet, no such signed receipt exists. As a result, the consumer can always claim that they didn't authorize the transaction. Such a claim is called a "chargeback." In the event of a chargeback, the merchant not only ends up losing the transaction amount, but generally also must pay a chargeback fee of $10-$25.

A sixth problem is that many previously proposed solutions to the problems cited require the consumer to physically possess a personalized, portable, man-made memory device—referred to in this specification as a "token"—to carry out a transaction. "Personalized" means that a token that contains in memory information that is in some way unique to the consumer. An example of personalized data include a credit card number, a checking account number, or any other unique account number. Example tokens include credit cards, debit cards, paper checks, and smart cards. A token can also be a PDA or wireless telephone that has programmed with information personalized to the consumer that is used to complete a financial transaction. The problems with requiring the use of a token to complete a financial transaction are numerous: the consumer must carry the token, which may be cumbersome; the loss or theft of a consumer's token financially incapacitates the consumer; and stealing a consumer's token may allow a thief to make fraudulent charges using the token. Tokenless transaction systems are known in the art; examples include U.S. Pat. No. 5,613,012 to Hoffman et al., U.S. Pat. No. 5,838,812 to Pare, Jr. et al., U.S. Pat. No. 5,870,723 to Pare, Jr. et al., U.S. Pat. No. 6,230,148 to Pare, Jr. et al., and U.S. Pat. No. 6,154,879 to Pare, Jr. et al., all of which are assigned to VeriStar Corporation, the assignee of the instant invention, and all of which are incorporated by reference.

As a result, there is a need for a new electronic financial transaction system that solves these problems for telephone and wireless PDA-style transactions. Accordingly, it is an object of this invention to provide a new system and method for biometric financial transactions.

In particular, it is an object of the invention that each transaction authorized using the invention cannot be repudiated by the consumer, thus eliminating chargebacks.

It is another object of the invention that the system and method be convenient for the consumer, eliminating the need to recite or otherwise enter credit card or other account numbers into a telephone or PDA.

It is another object of the invention that the system and method be secure, eliminating the possibility of fraud via intercepting transmissions from the telephone or PDA.

It is still another object of the invention that the system and method provide the flexibility of supporting multiple types of financial accounts, e.g., credit cards, debit cards, and checking (ACH) accounts.

It is another object of this invention that the consumer be able to complete a transaction on a tokenless basis. As such, this tokenless transaction occurs without the consumer being required to possess or present any man-made, portable devices which contain in memory data that is personalized to the consumer, i.e., tokens. Although the consumer may optionally possess such tokens, the invention is expressly designed to function without requiring their use and as such, the invention is designed to be tokenless.

It is yet another object of the invention that the system and method, through its superior security and non-repudiation capabilities, justify a reduced discount rate for the merchant.

It is still another object of the invention that it be easy to integrate with existing merchant computer, information, and payment systems.

SUMMARY OF THE INVENTION

This invention provides a method for tokenless biometric authorization of an electronic transaction between a consumer and a merchant using an electronic identicator and an access device. The method comprises the following steps: In a consumer registration step, a consumer registers with the electronic identicator at least one registration biometric sample taken directly from the consumer's person. In a first communications establishment step, the consumer and merchant establish communications with each other via an access device capable of biometric input, and wherein the access device is not required to contain in memory any data that is personalized to the consumer. In a proposal step, the merchant proposes a commercial transaction to the consumer via the access device. In a first access device identification step, the access device communicates to the merchant an identification code associated with the access device. In a second communications establishment step, after the consumer and merchant have agreed on the proposed commercial transaction, the consumer and the electronic identicator use the access device to establish communications with each other. In a second access device identification step, the access device communicates to the electronic identicator the identification code associated with the access device. In a consumer identification step, the electronic identicator compares a bid biometric sample taken directly from the consumer's person with at least one previously registered biometric sample to produce a successful or failed identification of the consumer. In an information forwarding step, upon successful identification of the consumer, the electronic identicator electronically forwards information regarding the consumer to the merchant. Upon successful identification of the consumer, these steps enable a biometrically authorized electronic financial transaction without the consumer being required to present any personalized man-made memory tokens.

Optionally, the electronic identicator may perform an electronic financial transaction authorization. In this embodiment, there is a transaction forwarding step, the merchant forwards information regarding the commercial transaction to the electronic identicator. In an identification code forwarding step, the merchant communicates to the electronic identicator the identification code associated with the access device that was previously communicated to the merchant. In an association step, the identification code associated with the access device is used to associate the biometric identification accomplished in the consumer identification step with the information regarding the commercial transaction. Finally, there is a financial transaction authorization step: the electronic identicator executes a financial transaction on behalf of the merchant.

Alternatively, the merchant may optionally perform an electronic financial transaction authorization. In this embodiment, there is an identification code forwarding step, wherein the electronic identicator forwards to the merchant the identification code associated with the access device that was previously communicated to the electronic identicator. In an association step, the identification codes associated with the access device are used to associate the information regarding the consumer with the commercial transaction. In a financial transaction authorization step, the merchant executes a financial transaction.

The invention also includes a system for tokenless biometric authorization of an electronic transaction between a consumer and a merchant. The system includes an electronic identicator, comprising at least one computer further comprising at least one database wherein the consumer registers at least one registration biometric sample taken directly from the consumer's person. It also includes an access device capable of establishing communications between the consumer and the merchant, and between the consumer and the electronic identicator, and further comprising biometric input means, said access device not being required to contain in memory any data that is personalized to the consumer. There is a communication means for enabling communications between the consumer and the merchant, and between the consumer and the electronic identicator, and capable of transmission of a bid biometric sample obtained by the access device from the person of the consumer to the electronic identicator. A comparator engine is used to compare a bid biometric sample to at least one registration biometric sample. An execution module is used for authorizing a transfer of a transaction amount from a financial account of the consumer to a financial account of the payor. The system enables a financial transaction to be conducted without the consumer being required to possess any man-made tokens containing information in memory that is personalized to the consumer.

The electronic identicator can include means responsive to a comparison matching the bid biometric sample to the registration biometric sample to forward information to the merchant regarding the consumer.

Information forwarded regarding the consumer may comprise a previously registered financial account identifier belonging to the consumer, or the consumer's age, or name, or address. It may also indicate the success or failure of a financial transaction. Financial account identifiers may comprise a credit card number, a debit card number, or a bank account number.

The access device may be a wireline telephone, a wireless telephone, a two-way pager, a personal digital assistant, or a personal computer. Identification codes associated with an access may include telephone numbers, electronic serial numbers (ESN), a hardware identification code, or encryption of a challenge message using a private key.

Communication of the identification code may be accomplished via caller ID, and the first and second communication establishment steps may be implemented using a telephone call, three-way calling, induced three-way calling, or packet switching.

Biometrics used in the invention may include finger images, facial images, retinal images, iris images, or voiceprints.

The execution module may optionally be located or operated by the merchant, or by the electronic identicator, or by a third party.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 1 shows the overall collection of elements comprising the system.

FIGS. 2, 3, and 4 illustrate examples of operation of the system of FIG. 1 according to the invention.

DETAILED DESCRIPTION

Overall Architecture

As shown in FIG. 1, the invention comprises the following components. There is at least one consumer who is able to use the invention for purchasing goods or services. Similarly, there is at least one merchant who is able to fulfill orders from the consumer. The consumer has access to an access device. As described in greater detail below, an access device is simply a device that is capable of both communicating an order to a merchant and also accepting a biometric from the consumer. A biometric or a biometric sample is any unique human characteristic of which a scan or image is taken directly from the person. The biometric or biometric sample may be, but is not limited to, any of the following: a voice print, a fingerprint, a retinal image, an iris image, a facial image.

A third-party identicator provides the ability to accept biometric and other data as input, to identify the consumer from this data, and to either complete a financial transaction on behalf of the merchant or to provide information to the merchant to enable the merchant to complete a financial transaction. Throughout this specification the terms "third-party identicator" and "electronic identicator" are used interchangeably; it is understood that the electronic identicator may be owned and/or operated by the merchant, the consumer, or a third party, without loss of generality.

Communication Links

Communication links exist or can be established between the access device and the merchant, the access device and the third-party identicator, and the merchant and the third-party identicator. A communication link can be a permanent connection (e.g., a leased line), a temporary switched-circuit connection (e.g., a dialup telephone call), or a virtual connection (e.g., via packet switching). Encryption can be employed on all communication links to protect sensitive data, as is standard in the industry.

Access Device

An access device is any device that is capable of communicating an order to a merchant and also accepting a biometric sample from the consumer. Different access devices are preferable in different situations. The access device is not required to contain in memory any data which is personalized to or unique to the consumer in order for the consumer to complete a financial transaction. Example access devices include:

A standard wireline telephone. A consumer can use such a device to call a merchant and place an order, as is done today. Additionally, it can be used as a biometric input device using the consumer's voice as a biometric.

A wireless or cellular telephone. Just like a standard wireline telephone, a wireless telephone can also be used as an access device using voice biometrics.

A wireless or cellular telephone with a built-in finger image scanner or other biometric sensor. This is like the example above, but uses a biometric other than voice, e.g., a finger image.

A wireless personal digital assistant (PDA) with a microphone or other biometric sensor. The wireless PDA can be used to enter and communicate an order to a merchant, and a microphone or other biometric sensor can be used to input a biometric. Other access devices will be apparent to those of ordinary skill in the art.

Every access device possesses an identification (ID) code. This ID code is preferably unique to the device, but is not required to be. Examples of ID codes include a digital certificate stored in a PDA or wireless telephone, a telephone or ESN number stored in a wireless telephone, or a telephone number in the case of a wire-line phone. Note that in this last example the ID code (the telephone number) is not unique to the device (the telephone) but is rather unique to the telephone line.

Third-Party Identicator

The third-party identicator is a data and call-processing center comprising a database of biometric and financial account information for at least one, and ordinarily for many consumers.

An identicator can be a single computer that serves a particular merchant or a large collection of computers that serve a number of different merchants. The third-party identicator accepts queries of biometric data and identifies consumers from this data. Once identified, the third-party identicator retrieves financial account data associated with that consumer. This financial account information either is then used to directly charge the financial account, or is provided to the merchant to charge the account.

Third-party identicators are known in the art; an example third-party identicator is given in section 1.5 "System Description: Data Processing Center" in U.S. Pat. No. 5,613,012 to Hoffman, et al., which is assigned to the same entity that this invention is assigned to, and which is hereby incorporated by reference.

Use of the System Via Telephone Access Device

In one embodiment a telephone is the access device used. Use of the system in this embodiment proceeds as follows.

1. The consumer uses the access device (telephone) to contact the merchant.

2. The consumer and the merchant work out and agree upon the details of the transaction, including the goods or services to be ordered, the ship to and bill to addresses, and the transaction amount.

3. The merchant receives the ID code from the access device. In one embodiment, this is via caller ID.

4. The merchant sends the ID code, the merchant identifying information, and the transaction amount to the third-party identicator. This information may be sent via an out-of-band channel (e.g., a separate network connection or via a virtual private network) or it may be passed in-band at the start of step S, below.

5. The merchant transfers the telephone call to the third-party identicator.

6. The third-party identicator prompts the consumer to enter their biometric. In one embodiment this biometric is a finger image. In another embodiment it is a voiceprint. Other biometrics are known. This biometric information is sent to the third-party identicator.

7. The third-party identicator uses the biometric information to identify the consumer. In the event that the consumer cannot be identified from the supplied biometric, the third-party identicator prompts the consumer to try again. If the consumer cannot be identified after repeated tries, the third-party identicator transfers the call to a human customer service assistant, who can use other means to identify the consumer.

8. In the event of a successful identification the third-party identicator retrieves account information for the consumer. Account information consists of credit card or other financial account data sufficient to complete a financial transaction.

9. If necessary, the third-party identicator uses the ID to assist in matching up the transaction information (merchant identification information and amount) with the individual.

10. In one embodiment, the third-party identicator performs a financial transaction using the retrieved financial account information. In another embodiment, the third-party identicator returns this financial account information to the merchant so that the merchant can complete a financial transaction.

Use of System Via Personal Digital Assistant

In another embodiment, a wireless PDA is the access device used. As discussed above, different biometrics are possible. For illustrative purposes, a voice biometric is used in this embodiment. Use of the system in this embodiment proceeds as follows:

1. The consumer uses the access device (wireless PDA) to contact the merchant's web site or its equivalent.

2. The consumer and the merchant work out and agree upon the details of the transaction, including the goods or services to be ordered, the ship to and bill to addresses, and the transaction amount.

3. The merchant receives the ID code from the access device. In this embodiment, this is either a digital certificate identification or a number stored in the device.

4. The merchant sends the ID code, the merchant identifying information, and the transaction amount to the third-party identicator.

5. The merchant sends a message to the device indicating that the device should contact the third-party identicator.

6. The third-party identicator sends a message to the device instructing it to prompt the consumer to enter his or her biometric. As described above, a voice biometric is used for illustrative purposes in this embodiment, but other biometrics are possible. This biometric information is sent to the third-party identicator.

7. The third-party identicator uses the biometric information to identify the consumer. In the event that the consumer cannot be identified from the supplied biometric, the third-party identicator prompts the consumer to try again. If the consumer cannot be identified after repeated tries, the third-party identicator alerts a human customer service assistant, who can use other means to identify the consumer.

8. In the event of a successful identification, the third-party identicator retrieves account information for the consumer. Account information may consist of credit card account number or other financial account data sufficient to complete a financial transaction.

9. If necessary, the third-party identicator uses the ID to assist in matching up the transaction information (merchant identification information and amount) with the individual.

10. In one embodiment, the third-party identicator performs a financial transaction using the retrieved financial account information. In another embodiment, the third-party identicator returns this financial account information to the merchant so that the merchant can complete a financial transaction.

Use of System Via Telephone with Induced Three-Way Calling

In another embodiment, a telephone having a feature known as "induced three-way calling is the access device used. In this embodiment, an external entity (e.g., the merchant) can request that the telephone put the current connection on hold and then dial out and establish another connection. While this feature does not exist in current generation telephones, implementation of such a feature would be straightforward for one of ordinary skill in the art. For illustrative purposes, a voice biometric is used in this embodiment. Use of the system in this embodiment proceeds as follows:

1. The consumer uses the access device (telephone) to contact the merchant.

2. The consumer and the merchant work out the details of the transaction, including the goods or services to be ordered, the ship to and bill to addresses, and the transaction amount.

3. The merchant receives the ID code from the access device. In one embodiment, this is via caller ID.

4. The merchant sends the ID code, the merchant identifying information, and the transaction amount to the third-party identicator. This information may be sent via an out-of-band channel (e.g., a separate network connection or via a virtual private network) or it may be passed in-band at the start of step S, below.

5. The merchant sends a message to the access device (telephone) instructing it to put the current call to the merchant on hold and to call the third-party identicator.

6. The third-party identicator obtains the access device ID from the access device. In one embodiment, this is via caller ID.

7. The third-party identicator prompts the consumer to enter their biometric. In one embodiment this biometric is a finger image. In another embodiment it is a voiceprint. Other biometrics are known. This biometric information is sent to the third-party identicator.

8. The third-party identicator uses the biometric information to identify the consumer. In the event that the consumer cannot be identified from the supplied biometric, the third-party identicator prompts the consumer to try again. If the consumer cannot be identified after repeated tries, the third-party identicator transfers the call to a human customer service assistant, who can use other means to identify the consumer.

9. In the event of a successful identification the third-party identicator retrieves account information for the consumer. Account information consists of credit card or other financial account data sufficient to complete a financial transaction.

10. If necessary, the third-party identicator uses the ID to assist in matching up the transaction information (merchant identification information and amount) with the individual.

11. In one embodiment, the third-party identicator performs a financial transaction using the retrieved financial account information. In another embodiment, the third-party identicator returns this financial account information to the merchant so that the merchant can complete a financial transaction.

12. The third-party identicator sends a message to the access device instructing it to terminate the call and resume the call with the merchant.

13. The merchant now verifies that the transaction completed successfully.

From the foregoing it will be appreciated how the objects of the invention are met. As can be seen from the above, the invention is marked advantageous over existing systems in numerous ways:

First, because each transaction is authorized using a biometric received from the consumer's person, the transaction cannot be repudiated, eliminating chargebacks.

Second, the invention is convenient for the consumer, in that the third-party identicator handles all financial account information, eliminating the need to recite or otherwise enter credit card or other account numbers into a telephone or PDA.

Third, the use of biometrics and encryption provides security, eliminating the possibility of fraud via intercepting transmissions from the telephone or PDA.

Fourth, the system supports the use of multiple types of financial accounts, providing flexibility for the consumer.

Fifth, through its superior security and non-repudiation capabilities, the invention justifies a reduced discount rate for the merchant.

Sixth, by using ordinary telephone connections or existing wireless connections, the invention is easy to integrate with existing merchant computer, information, and payment systems.

Seventh, the invention does not require the consumer to use or possess any portable, man-made tokens containing data personalized to the user in order to complete a financial transaction.

Although the invention has been described with respect to a particular biometric electronic transaction system and method for its use, it will be appreciated that various modifications of the system and method are possible without departing from the invention.

What is claimed is:

1. A method, comprising:
   receiving, via a communication link, at a data processing center:
      a biometric sample received from an individual, and
      a first request to use requested data of the individual, the first request being received from an entity device in communication with a wireless device operated by the individual, the first request including:
         a first wireless device identification code associated with the wireless device, and
         entity identifying information associated with the entity device;
   receiving, at the data processing center, a second request to use the requested data, wherein the second request is received by the data processing center from the wireless device via a separate communication link and includes a second wireless device identification code associated with the wireless device;
   performing a first comparison, at the data processing center, to determine whether the first wireless device identification code and the second wireless identification code match, and, if the first comparison yields a match, performing a second comparison
   at the data processing center, to determine whether the biometric sample received from the individual matches a registered biometric samples to produce a successful or failed result; and
   enabling, by the data processing center based upon a successful comparison, use of the data of the individual.

2. The method of claim 1, wherein the biometric sample is included in the first request.

3. The method of claim 1, wherein the biometric sample is included in the second request.

4. The method of claim 1, wherein the requested data includes one or more of: a name, an address, an age, and financial account data.

5. The method of claim 1, wherein the wireless device is one or more of: a wireless telephone, a two-way pager, a personal digital assistant, and a personal computer.

6. The method of claim 1, wherein the first and second a-wireless device identification codes are one or more of: a telephone number, an electronic serial number, a hardware identification code, and an encryption of a challenge message using a private key.

7. The method of claim 1, comprising associating, at the data processing center, the second request with the first request.

8. The method of claim 1, comprising receiving the first request from the entity to provide the entity with the requested data.

9. The method of claim 1, wherein the first request comprises transaction data and the data processing center performs a transaction by using the requested data.

10. A system, comprising:
    a data processing center that:
       receives, via a communication link, a biometric sample from an individual;
       receives, via the communication link, a first request to use requested data of the individual, the request being received from an entity device in communication with a wireless device operated by the individual, the first request including:
          a first wireless device identification code associated with the wireless device operated by the individual, and
          entity identifying information associated with the entity device;
       receives a second request to use the requested data, wherein the second request is received from the wireless device via a separate communication link and includes a second wireless device identification code associated with the wireless device;
       performs a first comparison to determine whether the first wireless device identification code and the second wireless identification code match, and, if the first comparison yields a match; performs a second comparison to determine whether the biometric sample received from the individual matches a registered biometric sample to produce a successful or failed result, wherein upon successful comparison, the requested data is authorized for use.

11. The system of claim 10, wherein the data processing center receives a transferred connection between the entity and the individual, wherein the wireless device of the individual is connected to the data processing center via the separate communication link.

12. The system of claim 10, wherein the data processing center initiates a prompt for the individual to present the biometric sample via the wireless device, wherein the data processing center initiates the prompt by determining the appropriate wireless device via a wireless device identification code associated with the wireless device.

13. The system of claim 10, wherein upon a successful comparison, the data processing center sends the requested data to the entity.

14. The system of claim 10, wherein upon a successful comparison, the data processing center performs a transaction using the requested data.

15. The system of claim 10, wherein upon an unsuccessful comparison, the data processing center denies use of the requested data.

16. A data processing center, comprising:
    a processor; and
    a memory, wherein the processor and memory are communicatively coupled to one another;

wherein the processor:
- receives, via a communication link, a request from an entity to use requested data of an individual, the request including first wireless device identification data received by the entity from a wireless device operated by the individual;
- receives, from the wireless device via a separate communication link, second wireless device identification data;
- determines if the received first and second wireless device identification data match;
- upon the determination of a successful match of the first and second wireless device identification data, compares biometric data to identify the individual; and
- responds to the request from the entity.

17. The data processing center of claim 16, comprising a database that stores data and one or more registered biometric samples that the individual has provided to the database.

18. The data processing center of claim 17, comprising a comparator engine that compares the one or more registered biometric samples to a biometric sample received from the wireless device, wherein a successful comparison of the one or more registered biometric samples with the received biometric sample enables use of the requested data.

19. The data processing center of claim 16, comprising a database that stores wireless device identification data, wherein the stored wireless device identification data is one or more of: a telephone number, an electronic serial number, a hardware identification code, and an encryption of a challenge message using a private key.

20. The data processing center of claim 19, wherein the stored wireless device identification data is associated with one or more registered biometric samples and the requested data.

21. The data processing center of claim 19, wherein the stored wireless device identification data is used to establish communication with the wireless device.

* * * * *